United States Patent [19]

Gutman

[11] 4,051,239
[45] Sept. 27, 1977

[54] METHOD OF USE AND PROCESS FOR PREPARING PHOSPHOROIMINOBENZOYLUREA INSECTICIDES

[75] Inventor: Arnold D. Gutman, Berkeley, Calif.

[73] Assignee: Stauffer Chemical Company, Westport, Conn.

[21] Appl. No.: 652,039

[22] Filed: Jan. 26, 1976

[51] Int. Cl.$^2$ .................. A01N 9/36; C07F 9/24
[52] U.S. Cl. .................. 424/211; 260/938; 260/984
[58] Field of Search .......... 260/938, 959, 969, 944, 260/984; 424/211

[56] References Cited
U.S. PATENT DOCUMENTS 3,845,176  10/1974  Weir .................. 260/938 X
3,846,514  11/1974  Schrader et al. .......... 260/938

Primary Examiner—Anton H. Sutto
Attorney, Agent, or Firm—M. Henry Heines; Daniel C. Block

[57] ABSTRACT

A composition of matter is described herein which has insecticidal activity and methods of use. The insecticide composition is defined by the following formula:

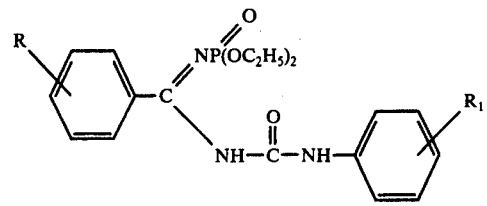

in which R and $R_1$ are independently selected from the group consisting of hydrogen, 2-halogen, 4-halogen, and 2,6-dihalogen. An additional composition of matter is described herein which is useful as an intermediate in the manufacture of the insecticide composition described above. The intermediate composition is defined by the following formula, in which R is as described above:

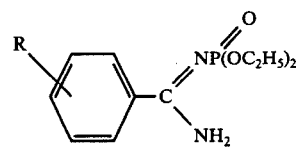

35 Claims, No Drawings

METHOD OF USE AND PROCESS FOR PREPARING PHOSPHOROIMINOBENZOYLUREA INSECTICIDES

SUMMARY OF THE INVENTION

The present invention relates to novel phosphoroiminobenzoylureas. More specifically, this invention relates to compounds of the formula

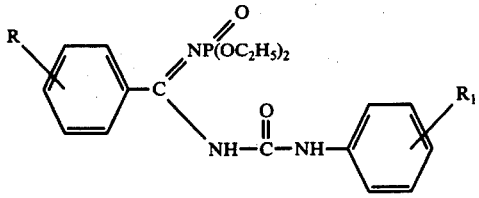

in which R and $R_1$ are independently selected from the group consisting of hydrogen, 2-halogen, 4-halogen, and 2,6-dihalogen.

The compounds of the present invention, as will appear from the data which follows, have utility as insecticides. These compounds have been found to show particular lepidoptericidal utility.

In another aspect, this invention relates to novel N-[α-amino-2-(substituted phenyl)benzylidene]0,0-diethylphosphoramidates, which are useful as intermediates in the manufacture of the phosphoroiminobenzoylureas described above. These intermediates have the following formula:

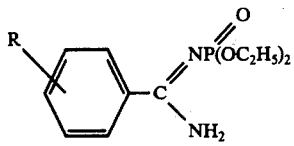

in which R is selected from the group consisting of hydrogen, 2-halogen, 4-halogen, and 2,6-dihalogen.

In a further aspect, this invention relates to a process for the manufacture of the phosphoroiminobenzoylureas described hereinabove, comprising reacting a compound having the formula

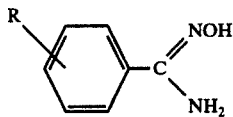

wherein R is defined above with approximately equimolar amounts of diethylchlorophosphite and a suitable organic base to produce the N-[α-amino-2-(substituted phenyl)benzylidene]0,0-diethylphosphoramidate described hereinabove, and reacting said phosphoramidate with an isocyanate having the formula

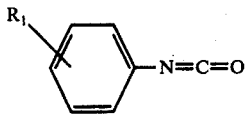

wherein $R_1$ is defined above to produce the end product.

DETAILED DESCRIPTION OF THE INVENTION

The compounds of the present invention can be prepared by the following general method, in which R and $R_1$ are as described above:

REACTION 1

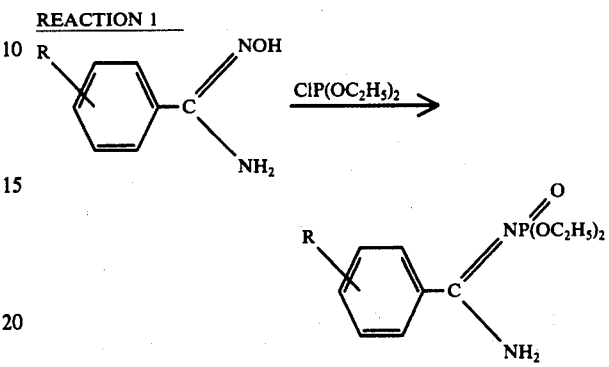

Generally, diethylchlorophosphite is combined with approximately equimolar amounts of the benzamide oxime and a suitable organic base in a suitable solvent while the reaction temperature is maintained at a low level, preferably between about −40° and about −20° C. Examples of a suitable organic base are triethylamine, pyridine, and dimethylaniline; and examples of a suitable solvent are diethylether and dry tetrahydrofuran.

REACTION 2

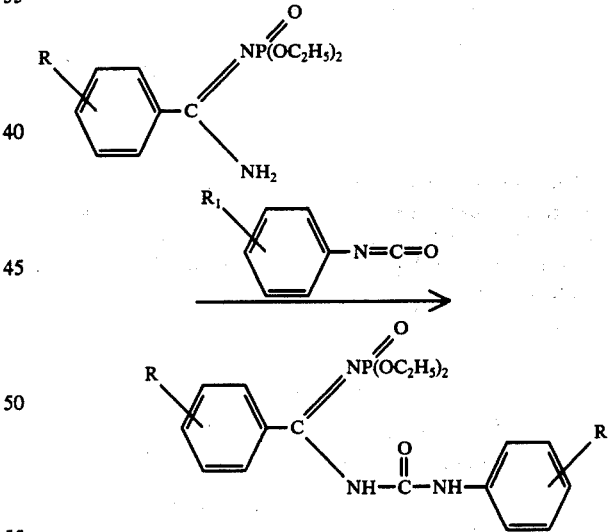

Approximately equimolar amounts of the phosphoramidate and the isocyanate are combined in a suitable solvent and heated to reflux. Examples of a suitable solvent for this reaction are toluene, benzene, xylene, and various chlorinated solvents. The product is recovered from the resulting mixture.

Alternatively, the benzamide oxime in Reaction 1 above is reacted with the isocyanate to produce the carbamyl benzamidoxime shown below:

REACTION 1'

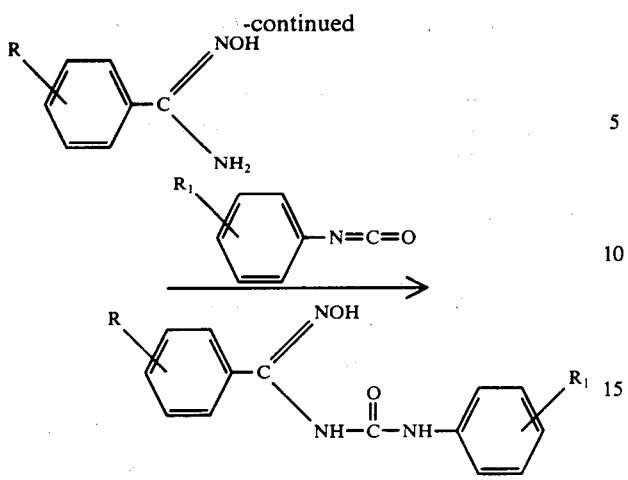

The above intermediate is a known compound. It is subsequently reacted with diethylchlorophosphite to produce the desired compound of the invention:

REACTION 2'

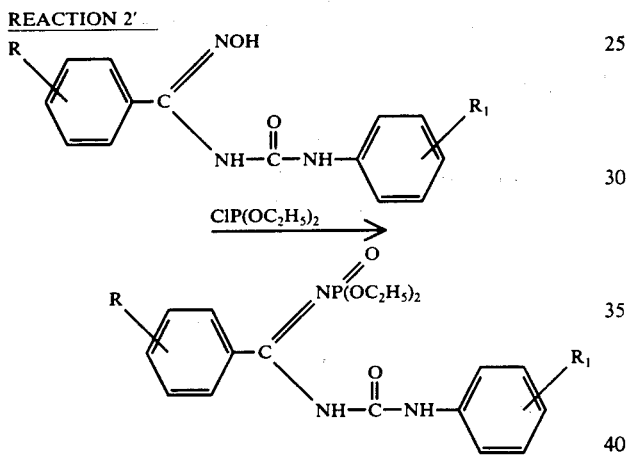

The examples shown herein are illustrative of the first method of preparation of the compounds of the invention as described above. For the balance of this specification, the following numbering system will be used for nomenclature:

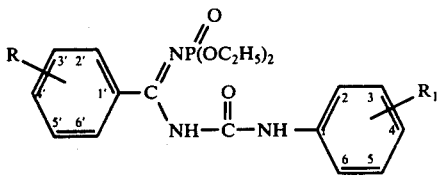

EXAMPLE I
N-(α-Amino-2-chlorophenylbenzylidene)0,0-diethyl-phosphoramidate (Compound No. 15)

In a 500 ml 3-neck flask fitted with a stirrer, thermometer, dropping funnel and condenser with drying tube, were combined 8.5 g (0.05 mole) of 0-chlorobenzamide oxime, 5.0 g (0.05 mole) of triethylamine and 200 ml of diethylether. The resulting solution was stirred and cooled to −20° C with a dry ice bath. Through the dropping funnel 7.8 g (0.05 mole) of diethylchlorophosphite was added over a period of 15 minutes while the reaction temperature was maintained at −20° to −22° C. After the addition was complete, the mixture was stirred at −20° C for 30 minutes, then at room temperature for 1 hour. The mixture was filtered free of salt and the solvent was removed in vacuo to yield 12.0 g. of the desired compound N-(α-amino-2-chloro-phenylbenzylidene)0,0-diethylphosphoramidate.

EXAMPLE II
1-(4-Chlorophenylcarbamyl)3-(0,0-diethylphos-phoro)2'-chlorobenzamidine (Compound No. 1)

In a 100 ml round bottom flask were combined 4.35 g (0.015 mole) of the product of Example I, 2.3 g (0.015 mole) of 4-chlorophenylisocyanate and 50 ml of toluene. The mixture was heated under reflux for 4 hours, then stripped in vacuo to yield 6.1 g of crude product. The crude yield was titrated with diethylether to yield 3.3 g of the desired product, m.p. 138°–141° C.

EXAMPLE III
1-(2,6-Dichlorophenylcarbamyl)3-(0,0-diethylphos-phoro)2'-chlorobenzamidine (Compound No. 2)

In the same manner as Example II, 4.0 g (0.0135 mole) of N-(α-amino-2-chlorophenylbenzylidene)0,0-diethyl-phosphoramidate, 2.55 g (0.0135 mole) of 2,6-dichlorophenylisocyanate and 50 ml of toluene were combined to yield 5.6 g of the desired compound, $n_D^{30}$ 1.5515.

Other compounds, such as those in the following tables, can be prepared in a manner analogous to that shown in the examples above, starting with the appropriate materials. The compounds in the tables are representative of those embodied in the present invention. Numbers have been assigned to the compound for purposes of identification throughout this specification.

TABLE I
Phosphoroiminobenzoylureas

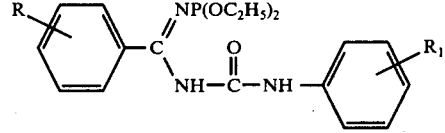

| Compound No. | R | $R_1$ | $n_D^{30}$ or melting point |
|---|---|---|---|
| 1 | 2-Cl | 4-Cl | 138–141° C |
| 2 | 2-Cl | 2,6-Cl | 1.5515 |
| 3 | 2,6-Cl | H | 1.5546 |
| 4 | 2,6-Cl | 4-Cl | 1.5523 |
| 5 | H | 2-Cl | 1.5103 |
| 6 | 2-Cl | 4-Br | glass * |
| 7 | 2,6-F | 4-Cl | 1.5238 |
| 8 | 2,6-F | 4-Br | 1.5133 |
| 9 | 4-Cl | 2,6-Cl | 1.5050 |
| 10 | 4-Cl | 4-Cl | glass * |
| 11 | 4-Cl | 2-Cl | 1.5252 |
| 12 | 2,6-F | 2-Cl | 123–128° C |

* glass : high viscosity oil

TABLE II
Intermediates

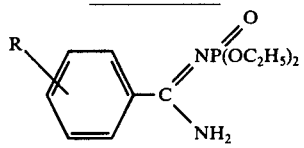

| Compound No. | R | $n_D^{30}$ or Description |
|---|---|---|
| 13 | 2-Cl | 1.5201 |
| 14 | 2,6-F | |
| 15 | 2,6-Cl | semi-solid |

TABLE II-continued

Intermediates

R─〈benzene ring〉─C(=NP(O)(OC₂H₅)₂)(NH₂)

| Compound No. | R | $n_D^{30}$ or Description |
|---|---|---|
| 16 | H | |
| 17 | 4-Cl | |

INSECTICIDAL EVALUATION

A. Housefly [*Musca domestica* (L.)] (HF)

Test compounds are diluted in acetone and aliquots are pipetted onto the bottom of 55 × 15 mm aluminum dishes. To insure even spreading of the chemical on the bottom of the dishes, 1 ml of acetone containing 0.02% peanut oil is also added to each dish. After all solvents have evaporated the dishes are placed in circular cardboard cages containing 25 female houseflies. The cages are covered on the bottom with cellophane and the top with tulle netting, and each contains a sugar-water saturated cotton plug for maintenance of the flies. Mortality is recovered after 48 hours. Test levels range from 100 μg/25 female houseflies down to that at which approximately 50% mortality occurs.

B. German Cockroach [*Blattella germanica* (Linné)] (GR)

Test compounds are diluted in a 50—50 acetone-water solution. Two cc of the solutions are sprayed through a DeVilbiss type EGA hand spray gun into circular cardboard cages containing 10 1-month-old German cockroach nymphs. The test cages are covered on the bottom with cellophane and the top with tulle netting. Percent mortality is recorded 7 days later. Test concentrations range from 0.1% down to that at which approximately 50% mortality occurs.

C. Lygus Bug [*Lygus hesperus* (Knight)] (LB)

Test compounds are in a 50—50 acetone-water solution. Two cc of the solutions are sprayed through a DeVilbiss type EGA hand spray gun into circular cardboard cages containing one string bean pod and 10 adult lygus bugs. The test cages are covered on the bottom with cellophane and the top with tulle netting. Percent mortality is recroded 48 hours later. Test concentrations range from 0.05% down to that at which approximately 50% mortality occurs.

D. Black Bean Aphid [*Aphis fabae* (Scop.)] (BA)

Nasturtium plants (*Tropaeolum sp.*), approximately 5 cm tall, are transplanted into sandy loam soil in 3-inch clay pots and infested with 25-50 black bean aphids of mixed ages. Twenty-four hours later they are sprayed, to the point of runoff, with 50—50 acetone-water solutions of the test chemicals. Treated plants are held in the greenhouse and mortality is recorded after 7 days. Test concentrations range from 0.05% down to that at which 50% mortality occurs.

E. Salt-Marsh Caterpillar [*Estigmene acrea* (Drury)] (SMC)

Test compounds are diluted in a 50—50 acetone-water solution. Sections of curly dock (*Rumex crispus*) leaves, approximately 1 × 1.5 inches, are immersed in the test solutions for 2-3 seconds and placed on a wire screen to dry. The dried leaves are placed in petri dishes containing a moistened piece of filter paper and infested with five second-instar salt-marsh larvae. Mortality of the larvae is recorded 48 hours later, and a piece of synthetic media is added to dishes containing survivors. These are then held for 5 additional days to observe for any delayed effects of the test chemicals. Test concentrations range from 0.05% down to that at which approximately 50% mortality occurs.

F. Cabbage Looper [*Trichoplusia ni* (Hübner)] (CL)

The test procedure is the same as that used for the Salt-Marsh Caterpillar above, except that cotyledons of hyzini squash (*Calabacita abobrinha*) are used rather than curly dock leaves.

G. Tobacco Budworm [*Heliothis virescens* (F.)] (TBW)

The test procedure is the same as that used for the Salt-Marsh Caterpillar above, except that sections of Romain lettuce (*Latuca sativa*) leaves are used rather than curly dock leaves.

H. Southern House Mosquito [*Culex pipiens quinquefasciatus* (Say)] (MOS)

Insecticidal activity is determined using third instar larvae of the mosquito *Culex pipiens quinquefasciatus*. Ten larvae are placed in a 6 ounce, number 67 Dixie wax paper cup containing 100 ml of an aqueous solution of the test chemical. The treated larvae are stored at 70° F, and 48 hours later the mortality is recorded. Test concentrations range from 0.5 ppm down to that at which approximately 50% mortality occurs.

The results of these tests using the compounds of Table I are listed in the following table. The values listed are the $LD_{50}$ values.

TABLE III

Insecticide Test Results

| Compound No. | HF (μg) | GR (%) | LB (%) | BA (%) | SMC (%) | CL (%) | TBW (%) | MOS (%) |
|---|---|---|---|---|---|---|---|---|
| 1 | >100 | >.1 | >.05 | >.05 | .0003 | >.1 | .01 | .3 |
| 2 | >100 | >.1 | .01 | .01 | .005 | >.1 | >.1 | >1 |
| 3 | 80 | >.1 | .03 | >.05 | >.05 | >.05 | >.1 | >1 |
| 4 | 100 | >.1 | .03 | >.05 | .005 | >.05 | >.1 | >1 |
| 5 | >100 | .05 | .01 | >.05 | .05 | >.1 | .1 | >1 |
| 6 | >100 | .1 | .03 | >.05 | .001 | .05 | .05 | .2 |
| 7 | >100 | — | — | >.05 | .0001 | .05 | >.1 | .2 |
| 8 | >100 | >.1 | .03 | .03 | .01 | .1 | .1 | >1 |
| 9 | 100 | .1 | .03 | .01 | >.05 | >.05 | — | >1 |
| 10 | >100 | .1 | .025 | >.05 | >.05 | >.05 | >.1 | >1 |
| 11 | >100 | >.1 | .05 | >.05 | >.05 | >.05 | >.1 | >1 |
| 12 | >100 | >.1 | >.05 | >.05 | >.05 | .1 | >.1 | >1 |

The compounds of this invention are generally embodied in a form suitable for convenient application. For example, the compounds can be embodied in insecticidal compositions in the form of emulsions, suspensions, solutions, dusts, and aerosol sprays. In addition to the active compounds such compositions generally contain the adjuvants which are normally found in insecticide preparations. One such composition can contain either a single insecticidally active compound or a combination of insecticidally active compounds. The insecticide compositions of this invention can contain as adjuvants organic solvents such as sesame oil, xylene, or heavy petroleum; water, emulsifying agents, surface active agents, talc, pyrophyllite, diatomite, gypsum, clays, or propellants such as dichlorodifluoromethane, or a combination of these. If desired, however, the active compounds can be applied directly to feedstuffs, seeds, or other such matter upon which the pests feed. When applied in such a manner, it will be advantageous to use a compound which is not volatile. In connection with the activity of the presently disclosed insecticide compounds, it should be fully understood that the compounds need not be active as such. The purposes of this invention will be fully served by a compound which is rendered active by an external influence such as light, or by some physiological action which the compound induces when it is ingested into the body of the insect.

The precise manner in which the insecticidal compounds of this invention should be used in any particular instance will be readily apparent to a person skilled in the art. The concentration of the active insecticide in a typical composition can vary within rather wide limits. Ordinarily, the insecticide will comprise not more than about 15.0% by weight of the composition. The preferred range of concentration of the insecticide is about 0.1 to about 1.0% by weight.

What is claimed is:
1. A compound having the formula

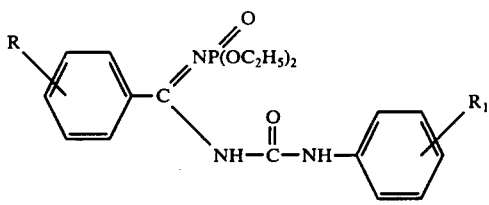

in which R and $R_1$ are independently selected from the group consisting of hydrogen, 2-halogen, 4-halogen, and 2,6-dihalogen.

2. A compound according to claim 1 in which R is 2-chloro and $R_1$ is 4-chloro.
3. A compound according to claim 1 in which R is 2-chloro and $R_1$ is 2,6-dichloro.
4. A compound according to claim 1 in which R is 2,6-dichloro and $R_1$ is hydrogen.
5. A compound according to claim 1 in which R is 2,6-dichloro and $R_1$ is 4-chloro.
6. A compound according to claim 1 in which R is hydrogen and $R_1$ is 2-chloro.
7. A compound according to claim 1 in which R is 2-chloro and $R_1$ is 4-bromo.
8. A compound according to claim 1 in which R is 2,6-difluoro and $R_1$ is 4-chloro.
9. A compound according to claim 1 in which R is 2,6-difluoro and $R_1$ is 4-bromo.
10. A compound according to claim 1 in which R is 4-chloro and $R_1$ is 2,6-dichloro.
11. A compound according to claim 1 in which R is 4-chloro and $R_1$ is 4-chloro.
12. A compound according to claim 1 in which R is 4-chloro and $R_1$ is 2-chloro.
13. A compound according to claim 1 in which R is 2,6-difluoro and $R_1$ is 2-chloro.
14. A method of controlling insects comprising applying to the habitat thereof an insecticidally effective amount of a compound having the formula

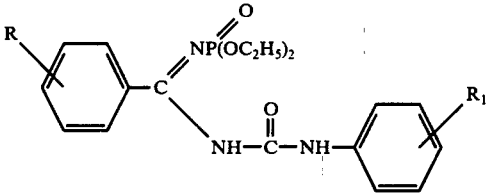

in which R and $R_1$ are independently selected from the group consisting of hydrogen, 2-halogen, 4-halogen, and 2,6-dihalogen.

15. A method according to claim 14 in which R is 2-chloro and $R_1$ is 4-chloro.
16. A method according to claim 14 in which R is 2-chloro and $R_1$ is 2,6-dichloro.
17. A method according to claim 14 in which R is 2,6-dichloro and $R_1$ is hydrogen.
18. A method according to claim 14 in which R is 2,6-dichloro and $R_1$ is 4-chloro.
19. A method according to claim 14 in which R is hydrogen and $R_1$ is 2-chloro.
20. A method according to claim 14 in which R is 2-chloro and $R_1$ is 4-bromo.
21. A method according to claim 14 in which R is 2,6-difluoro and $R_1$ is 4-chloro.
22. A method according to claim 14 in which R is 2,6-difluoro and $R_1$ is 4-bromo.
23. A method according to claim 14 in which R is 4-chloro and $R_1$ is 2,6-dichloro.
24. A method according to claim 14 in which R is 4-chloro and $R_1$ is 4-chloro.
25. A method according to claim 14 in which R is 4-chloro and $R_1$ is 2-chloro.
26. A method according to claim 14 in which R is 2,6-difluoro and $R_1$ is 2-chloro.
27. A compound having the formula

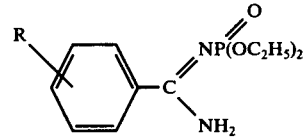

in which R is selected from the group consisting of hydrogen, 2-halogen, 4-halogen, and 2,6-dihalogen.

28. A compound according to claim 27 in which R is 2-chloro.
29. A compound according to claim 27 in which R is 2,6-dichloro.
30. A process for the manufacture of a compound having the formula

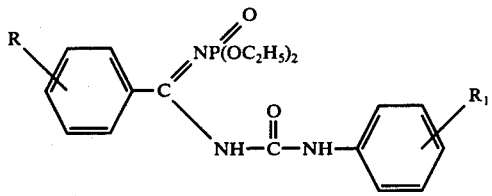

wherein R and $R_1$ are independently selected from the group consisting of hydrogen, 2-halogen, 4-halogen, and 2,6-dihalogen comprising
a. reacting a compound having the formula

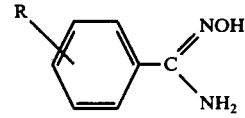

wherein R is defined above with diethyl chlorophosphite and a suitable organic base to produce a compound having the formula

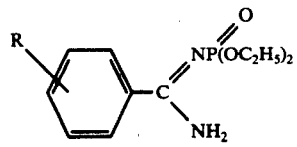

and b. reacting the product of step (a) with a compound having the formula

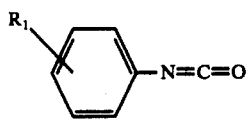

wherein $R_1$ is defined above to produce the end product.

31. A process according to claim 30 in which the reaction of step (a) takes place at between about $-40°$ C and about $-20°$ C.

32. A process according to claim 30 in which the organic base of step (a) is selected from the group consisting of triethylamine, pyridine, and dimethylaniline.

33. A process according to claim 30 in which the solvent of step (a) is diethylether or tetrahydrofuran.

34. A process according to claim 30 in which the solvent of step (a) is selected from the group consisting of toluene, benzene, xylene, and chlorinated solvents.

35. A process according to claim 30 in which the reaction of step (a) is conducted at the reflux temperature of the mixture.